United States Patent
Mayenberger et al.

[11] Patent Number: 5,964,779
[45] Date of Patent: Oct. 12, 1999

[54] SURGICAL TUBULAR-SHAFTED INSTRUMENT

[75] Inventors: Rupert Mayenberger, Rielasingen; Pedro Morales, Tuttlingen; Dieter Weisshaupt, Immendingen, all of Germany

[73] Assignee: Aesculap AG & Co. KG, Tuttlingen, Germany

[21] Appl. No.: 09/107,005

[22] Filed: Jun. 30, 1998

[30] Foreign Application Priority Data

Jul. 2, 1997 [DE] Germany ............ 197 28 114

[51] Int. Cl.$^6$ .................................................. A61B 17/00
[52] U.S. Cl. .................... 606/205; 606/174; 600/564
[58] Field of Search ............... 606/51, 52, 190, 606/171, 174, 205–210; 600/564–570

[56] References Cited

U.S. PATENT DOCUMENTS

| | | |
|---|---|---|
| 4,712,545 | 12/1987 | Honkanen . |
| 5,275,613 | 1/1994 | Haber et al. ............ 606/205 |
| 5,509,923 | 4/1996 | Middleman et al. . |
| 5,582,617 | 12/1996 | Klieman et al. ............ 606/205 |

*Primary Examiner*—Michael Buiz
*Assistant Examiner*—William Lewis
*Attorney, Agent, or Firm*—Barry R. Lipsitz; Ralph F. Hoppin

[57] ABSTRACT

In a surgical tubular-shafted instrument comprising a tubular shaft and a gripping part connected thereto, a tool pivotable about an axis of rotation extending transversely to the longitudinal axis of the shaft, and a push element in the shaft, the push element being movable by the gripping part in the longitudinal direction of the shaft and being in engagement with the tool by using projections and recesses arranged in spaced relation to the axis of rotation of the tool such that the tool is pivotable about its axis of rotation upon displacement of the push element, in order to make higher loading possible with small dimensions, it is proposed that a ring-shaped cage be arranged on the push element and surround the axis of rotation of the tool and the point of engagement of the projection and the recess, and the inside wall of the cage carry the projection or the recess of the push element.

12 Claims, 5 Drawing Sheets

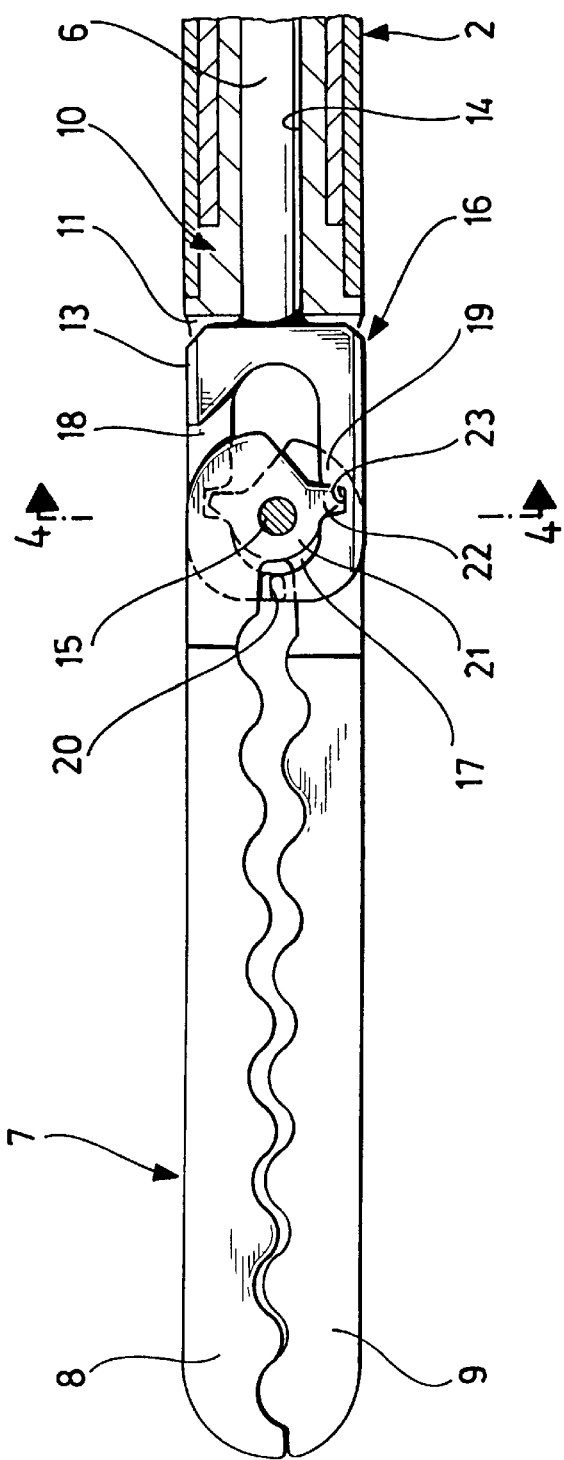
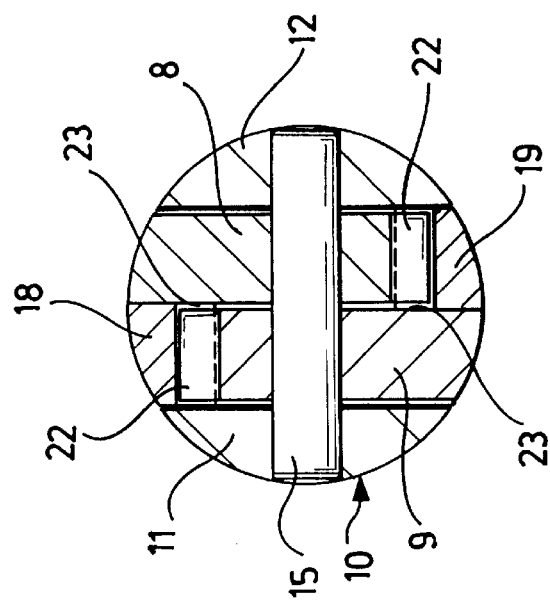

SURGICAL TUBULAR-SHAFTED INSTRUMENT

BACKGROUND OF THE INVENTION

The invention relates to a surgical tubular-shafted instrument comprising a tubular shaft and a gripping part connected thereto, a tool pivotable about an axis of rotation extending transversely to the longitudinal axis of the shaft, and a push element in the shaft, the push element being movable by the gripping part in the longitudinal direction of the shaft and being in engagement with the tool by means of projections and recesses arranged in spaced relation to the axis of rotation of the tool such that the tool is pivotable about its axis of rotation upon displacement of the push element.

Such surgical tubular-shafted instruments are known, for example, from U.S. Pat. No. 5,509,923. For pivotal movement of the two parts of the tool, these carry a toothed segment which meshes with an elongate toothed segment on the push element and thus transforms the translational movement of the push element into a rotational movement of the tool parts.

Tubular-shafted instruments of this kind often have a very small diameter and, therefore, it is difficult to achieve the necessary stability with such small diameters. With such tubular-shafted instruments, it thus often proves impossible to generate the desired closing forces for the tool.

With the known tubular-shafted instrument construction, there is, in particular, the danger that the operative connection between the projections and the recesses will become disengaged by deformation of the material used. The meshing projections and recesses may "snap out" or become completely disengaged.

SUMMARY OF THE INVENTION

The object of the invention is to so design a generic tubular-shafted instrument that in spite of small dimensions, large torques can be transmitted onto the tools in a reliable way.

This object is accomplished with a tubular-shafted instrument of the kind described at the outset, in accordance with the invention, in that a ring-shaped cage is arranged on the push element and surrounds the axis of rotation of the tool and the point of engagement of the projection and the recess, and the inside wall of the cage carries the projection or the recess of the push element.

Use of a ring-shaped cage, i.e., a self-contained component, results in a substantially increased stability of the operative surfaces of the push element and thus ensures that deformation of these parts transforming the push movement into a rotational movement does not occur even in the event of heavy loading. The projections and recesses are located in the interior of the cage, and so deviation of the corresponding parts outwards is excluded by the cage construction.

In principle, the tool can comprise a single pivotable part. In a particularly preferred embodiment, however, provision is made for the tool to comprise two parts which are pivotable coaxially and in opposite directions and are both in operative connection with the cage by means of projections or recesses in the interior of the cage of the push element.

Arrangement of the projection on the cage or on the tool is optional. It is merely essential that a projection and a recess be in operative connection with one another.

In a preferred embodiment, for example, projections and recesses can be formed by toothed segments, however, it is equally well possible to provide only a single projection engaging in a recess.

In the case of tool parts which are pivotable in opposite directions, it is advantageous for the cage to have two longitudinal arms lying alongside one another, with each of the longitudinal arms carrying a projection or a recess for one of the two parts, for the two parts to be mounted adjacent to one another for pivotal movement about the axis of rotation, and for one respective part and one respective longitudinal arm to lie in one plane and to be in operative connection with one another.

This results in a particularly space-saving assembly, for the parts of the tool can lie adjacent to one another, and the longitudinal arms of the push element then each lie in the plane of the tool part associated therewith, while the respective other tool part can be pivoted past the longitudinal arms.

It is also expedient for the longitudinal arms to be connected to one another at their free end by a bridge extending transversely to their longitudinal direction. This bridge closes off the interior surrounded by the longitudinal arms and thus forms the self-contained cage.

In this case, self-contained does not mean that the cage is closed on all sides thereof, but only that the cage is closed in the form of a ring. It is readily possible for the cage to be open at the sides. Ring-shaped is to be understood in a general sense. The shape of the interior of the cage may vary, the shape of an elongate hole being, for example, expedient.

In a preferred embodiment, the cage is guided for longitudinal movement between two bearing arms of the shaft which hold a bearing shaft for the tool between them. These bearing arms thus simultaneously serve to secure the cage and the push element connected to the cage against rotation.

The following description of preferred embodiments of the invention serves in conjunction with the accompanying drawings to explain the invention in greater detail. The drawings show:

BRIEF DESCRIPTION OF THE DRAWINGS

FIG. 3 a view similar to FIG. 2 in the closed position;

FIG. 4 a sectional view along line 4—4 in FIG. 3;

DETAILED DESCRIPTION OF THE INVENTION

Figure 1:
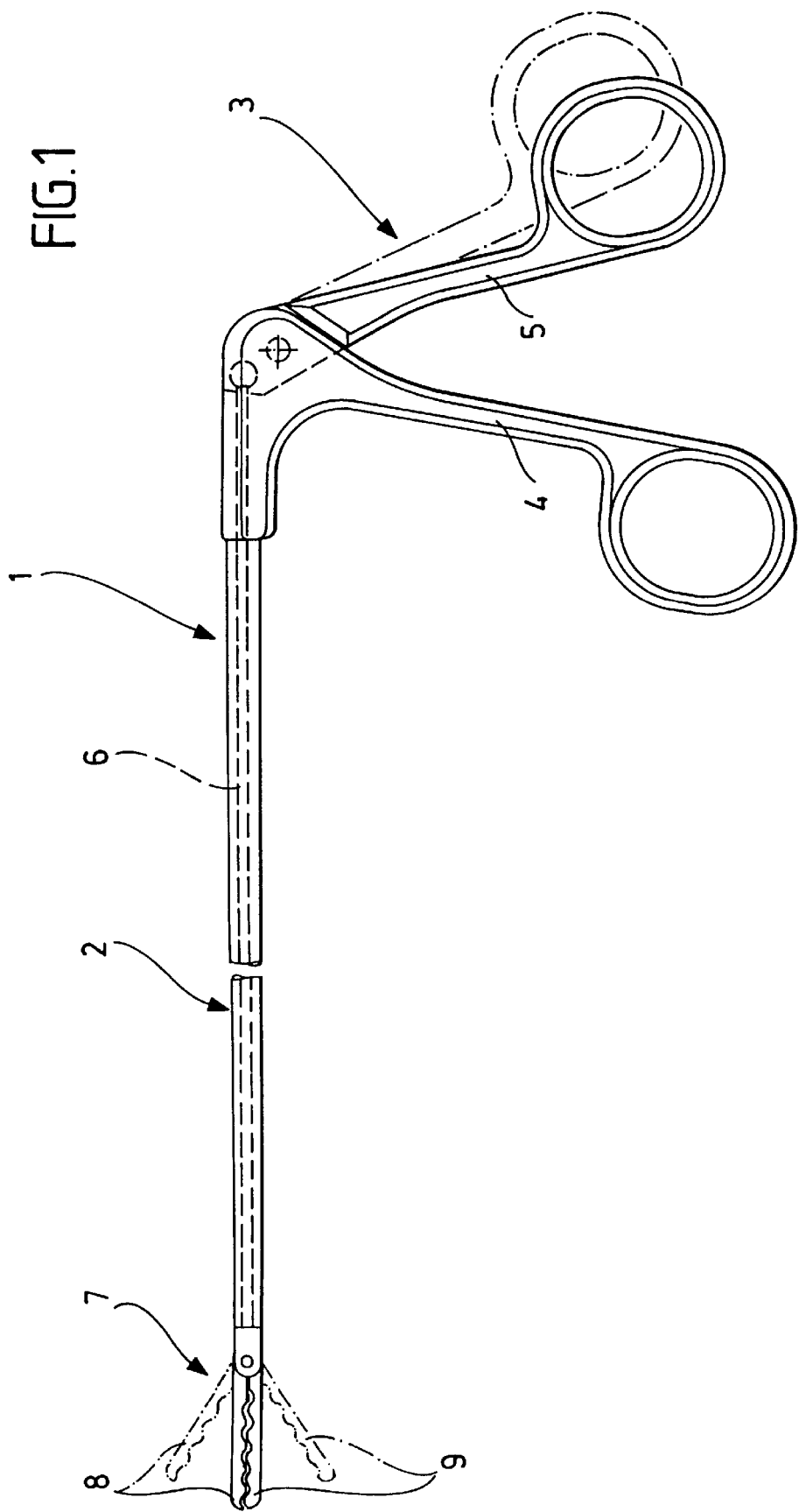
FIG. 1 a schematic side view of a tubular-shafted instrument with a pivotable tool.
Figure 2:
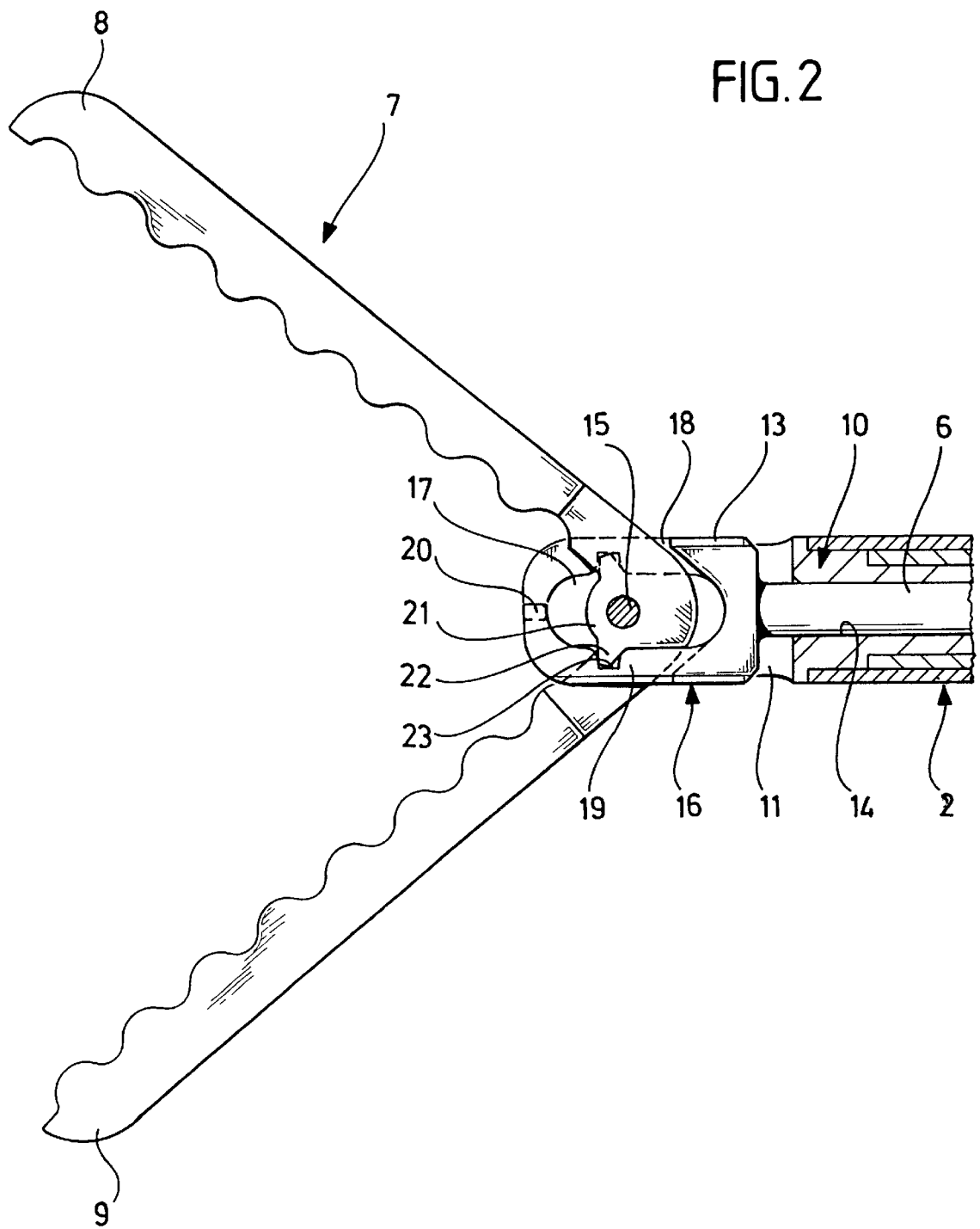
FIG. 2 an enlarged detailed view in longitudinal section of the tool area with two tool parts pivotable relative to each other in the open position.

The tubular-shafted instrument 1 shown in the drawings comprises an elongate, tubular shaft 2 and a gripping part 3 having a handle 4 fixedly connected to the shaft 2 and a handle 5 mounted for pivotal movement relative to the shaft 2. The handle 5 is articulatedly connected to a rod-shaped push element 6 in the interior of the shaft 2. The push element 6 is movable within the shaft 2 in the longitudinal direction thereof when the handle 5 is pivoted relative to the stationary handle 4.

A tool 7 is mounted at the free end of the shaft 2 for pivotal movement about an axis of rotation extending transversely to the longitudinal direction of the shaft 2. In the illustrated embodiment, the tool 7 comprises two tool parts 8, 9 which are pivotable in opposite directions. The tool parts are pivoted by the push element 6 between a closed position (in solid lines in FIG. 1) and an open position (in dot-and-dash lines in FIG. 1), and the translational movement of the push element is transformed by suitable gear means into a rotational movement of the tool parts 8, 9.

A bearing member 10 inserted into the free end of the shaft 2 closes the shaft 2 at the free end thereof. This bearing member 10 comprises two bearing arms 11, 12 extending in parallel alongside each other in the longitudinal direction of the shaft 2. The bearing arms 11, 12 retain a spacing between them and thereby form a receiving space 13 which is open in the upward, downward and forward directions and communicates with the interior of the shaft 2 through a central channel 14 in the bearing member 10.

A bearing shaft 15 on which the two tool parts 8, 9 are rotatably mounted adjacent to each other is held between the two bearing arms 11, 12 and extends transversely through the receiving space 13. The bearing shaft 15 thus defines the axis of rotation of the tool parts 8, 9.

The width of the tool parts 8, 9 is half the size of the width of the receiving space 13 so the tool parts 8, 9 thus also assume a defined position in the direction of the bearing shaft 15.

Figure 5:
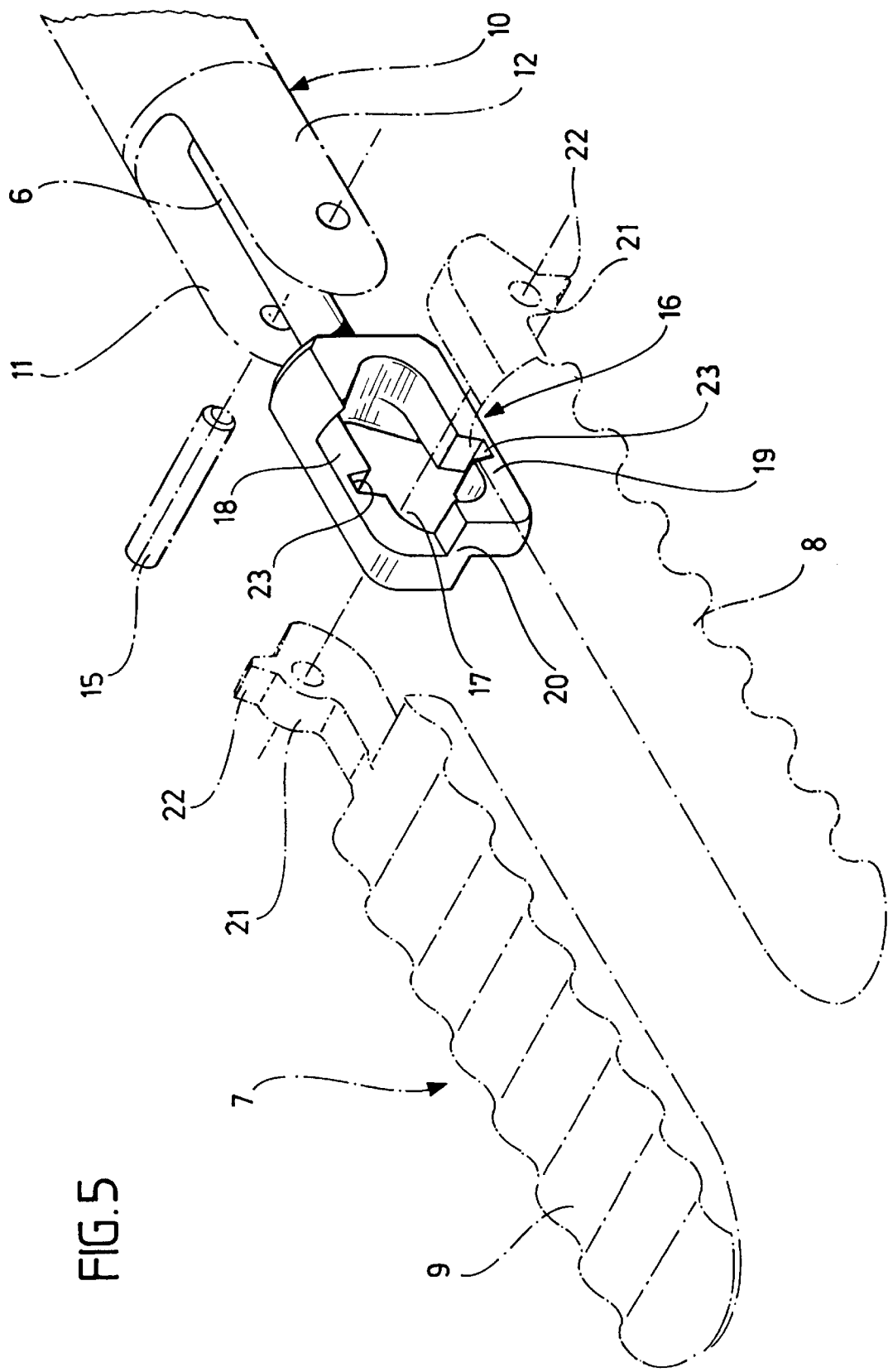
FIG. 5 a perspective view of the cage of the embodiment of FIGS. 1 to 4 surrounding the bearing point of the tool parts.

The rod-shaped push element 6 extends through the central channel 14 into the receiving space 13 where it is integrally connected to an essentially block-shaped cage 16 whose width corresponds to the width of the receiving space 13. This cage 16 (FIG. 5) has an elongate-hole-type opening 17 extending essentially over its entire length, thereby forming an upper longitudinal arm 18 and a lower longitudinal arm 19 which are connected to each other at their free ends.

The width of the longitudinal arms 18 and 19 is only half the size of the width of the cage 16 in total, and the longitudinal arms 18 and 19 are offset laterally from each other so the joining of the two longitudinal arms 18 and 19 is effected at the free end thereof by a bridge 20 extending transversely.

The cage 16 surrounds the bearing shaft 15. The upper longitudinal arm 18 is arranged above the tool part 9, the lower longitudinal arm 19 below the tool part 8 (FIG. 4).

The tool parts 8 and 9 surround the bearing shaft 15 in the form of a ring 21 which in the embodiment of FIGS. 1 to 5 carries a radially protruding projection 22. This projection 22 fits into a recess 23 in the longitudinal arm of the cage 16 lying in the plane of the respective tool part. This fitting is in the manner of engagement of teeth of a toothed gearing. Longitudinal movement of the cage 16 thus causes the ring 21 of the respective tool part to be taken along and the tool part to be pivoted about the axis of rotation formed by the bearing shaft 15. The tool parts are pivoted in opposite directions. When, for example, in the illustrated embodiment, the cage 16 is pushed forwards, the two tool parts are opened, when, on the other hand, the cage 16 is pushed back, they are closed.

The cage 16 is non-rotatably guided in the longitudinal direction between the two bearing arms 11, 12 and together with the tool parts 8, 9 fills out the receiving space 13 between the bearing arms 11, 12.

Owing to the design of the cage 16 as a self-contained body, deformation of the longitudinal arms 18, 19 is also excluded when high torques are transmitted via the operative connection between projection 22 and recess 23. The engagement of the projection 22 in the recess 23 is thus also maintained upon high loading.

In the embodiment of FIGS. 1 to 5, the tool parts 8, 9 each carry a projection 22 which engages in a recess 23 of the cage 16.

Figure 6:
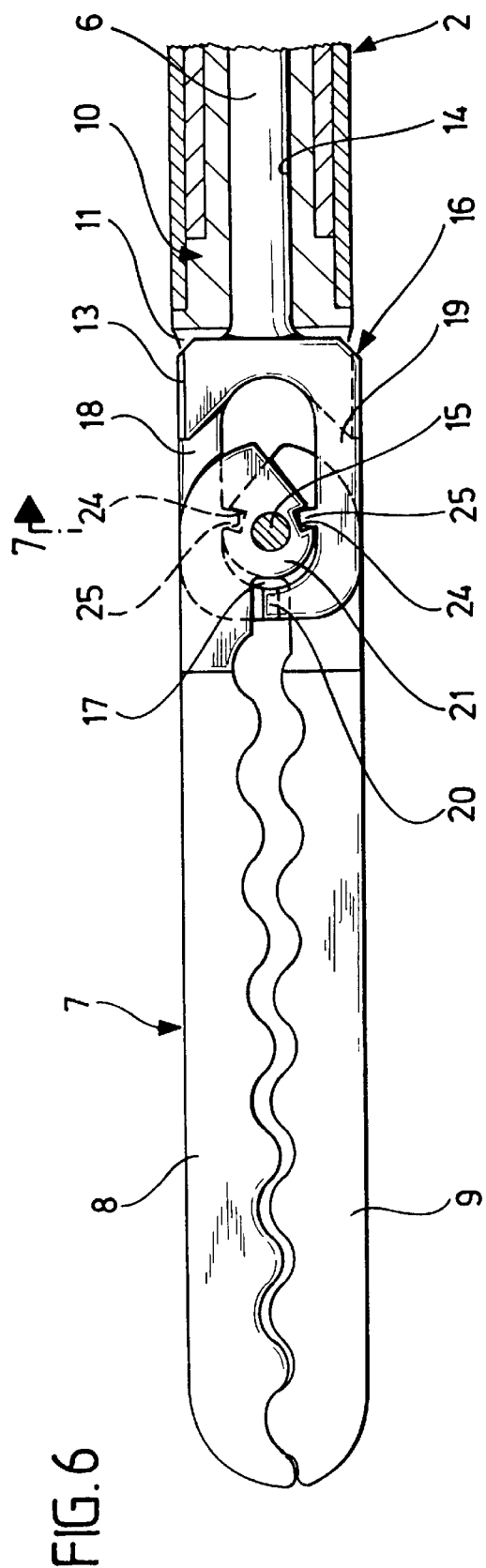
FIG. 6 a view similar to FIG. 3 of a tubular-shafted instrument in which projection and recess on cage and tool parts are exchanged in relation to the embodiment of FIGS. 1 to 5.
Figure 7:
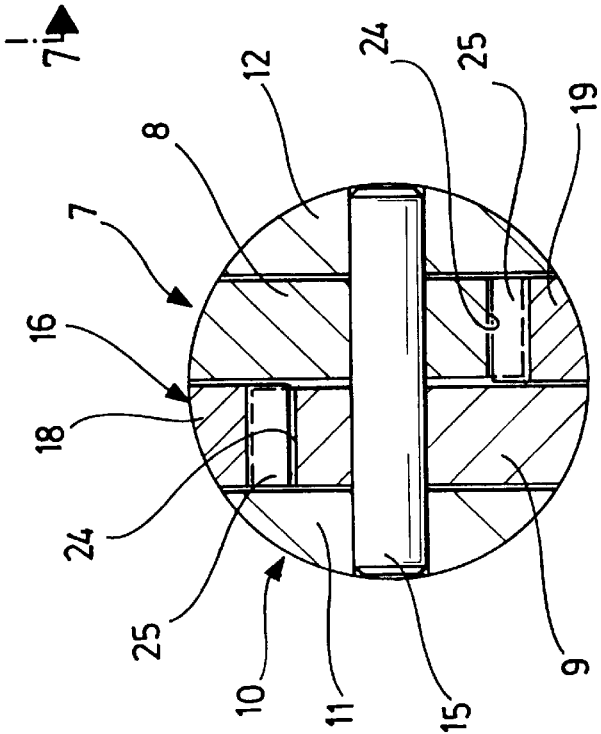
FIG. 7 a sectional view along line 7—7 in FIG. 6.

In the embodiment of FIGS. 6 and 7, which is otherwise of identical construction, and in which like parts, therefore, have like reference numerals, this arrangement is reversed. In this case, the tool parts 8, 9 have recesses 24 in which projections 25 on the cage 16 engage.

In the illustrated embodiments, the operative engagement between the tool parts, on the one hand, and the cage, on the other hand, is effected by only one projection and one recess, respectively. Alternatively, it is readily possible to also have toothed segments mesh with one another. This is particularly advantageous when larger pivotal movements of the tool parts are desired.

What is claimed is:

1. A surgical tubular-shafted instrument, comprising:
    a tubular shaft and a gripping part connected thereto,
    a tool pivotable about an axis of rotation extending transversely to a longitudinal axis of said shaft,
    a push element in said shaft,
    said push element being movable by said gripping part in the longitudinal direction of said shaft, and
    a ring-shaped cage arranged on said push element, said cage surrounding the axis of rotation of said tool, wherein:
        said push element is in engagement with said tool by means of at least one projection that engages at least one corresponding recess at a point of engagement to enable said tool to pivot about its axis of rotation upon displacement of said push element,
        said at least one projection and said at least one corresponding recess are arranged in spaced relation to the axis of rotation of said tool,
        said ring-shaped cage surrounds the point of engagement, and
        an inside wall of said cage carries said projection or said recess.

2. An instrument as defined in claim 1, wherein:
    said tool comprises two parts which are pivotable coaxially and in opposite directions, and are both in operative connection with said cage by means of the at least one projection or the at least one corresponding recess.

3. An instrument as defined in claim 2, wherein:
    said cage has two longitudinal arms lying alongside one another,
    one of said longitudinal arms carries the projection for one of said two parts,
    the other of said longitudinal arms carries the recess for the other of said two parts,
    said two parts are mounted adjacent to one another for pivotal movement about the axis of rotation, and
    one respective part and one respective longitudinal arm lie in one plane and are in operative connection with one another.

4. An instrument as defined in claim 3, wherein:
    said longitudinal arms are connected to one another at their free end by a bridge extending transversely to their longitudinal direction.

5. An instrument as defined in claim 1, wherein:

said cage is guided for longitudinal movement between two bearing arms of said shaft which hold a bearing shaft for said tool between them.

6. An instrument as defined in claim 2, wherein:

said cage is guided for longitudinal movement between two bearing arms of said shaft which hold a bearing shaft for said tool between them.

7. An instrument as defined in claim 3, wherein:

said cage is guided for longitudinal movement between two bearing arms of said shaft which hold a bearing shaft for said tool between them.

8. An instrument as defined in claim 4, wherein:

said cage is guided for longitudinal movement between two bearing arms of said shaft which hold a bearing shaft for said tool between them.

9. An instrument as defined in claim 1, wherein:

said projection and recess in operative connection with one another are formed by toothed segments.

10. An instrument as defined in claim 2, wherein:

said projection and recess in operative connection with one another are formed by toothed segments.

11. An instrument as defined in claim 1, wherein:

said push element is in engagement with said tool by means of at least a first projection that engages a corresponding first recess at a first point of engagement, and a second projection that engages a corresponding second recess at a second point of engagement, to enable said tool to pivot about its axis of rotation upon displacement of said push element.

12. An instrument as defined in claim 1, wherein:

said push element remains in engagement with said tool by means of said at least one projection that engages said at least one corresponding recess at said point of engagement throughout a range of motion of the push element in the longitudinal direction of said shaft.

* * * * *